United States Patent
Steinhofer

(10) Patent No.: US 11,918,416 B2
(45) Date of Patent: Mar. 5, 2024

(54) ULTRASOUND PROBE HANGER AND METHOD FOR SUSPENDING A WIRELESS ULTRASOUND TRANSDUCER WITHIN A CHAMBER OF AN ULTRASOUND TRANSDUCER HIGH-LEVEL DISINFECTION (HLD) SYSTEM

(71) Applicant: GE Precision Healthcare LLC, Wauwatosa, WI (US)

(72) Inventor: Franz Josef Steinhofer, Ampflwang (AT)

(73) Assignee: GE Precision Healthcare LLC, Waukesha, WI (US)

( * ) Notice: Subject to any disclaimer, the term of this patent is extended or adjusted under 35 U.S.C. 154(b) by 330 days.

(21) Appl. No.: 17/215,264

(22) Filed: Mar. 29, 2021

(65) Prior Publication Data

US 2022/0304655 A1    Sep. 29, 2022

(51) Int. Cl.
*A61B 8/00* (2006.01)
*A61B 50/20* (2016.01)

(52) U.S. Cl.
CPC .......... *A61B 8/4218* (2013.01); *A61B 8/4422* (2013.01); *A61B 8/4472* (2013.01); *A61B 50/20* (2016.02)

(58) Field of Classification Search
CPC ...... A61B 8/4422; A61B 8/4472; A61B 50/20
See application file for complete search history.

(56) References Cited

U.S. PATENT DOCUMENTS

2008/0064960 A1*  3/2008  Whitmore ................ A61N 7/02
                                                  600/459

FOREIGN PATENT DOCUMENTS

CN    210697678      *  6/2020   ............... A61B 8/00
WO    2022011430 A1    12/2015

* cited by examiner

*Primary Examiner* — Rochelle D Turchen
(74) *Attorney, Agent, or Firm* — McAndrews, Held & Malloy, Ltd.; Daniel Bissing; David Bates

(57) ABSTRACT

An ultrasound probe hanger includes a stem, shoulders, arms, and a probe holder. The shoulders are arranged generally perpendicular to the stem and are connected to a proximal end of the stem. The arms are arranged generally parallel to each other and to the stem. The arms are connected at upper ends to outer shoulder ends of the shoulders. The probe holder includes outer side portions, a rear portion, a partially open front portion, and four protrusions. The outer side portions are each connected to lower ends of the arms. The rear portion extends between the outer side portions. The partially-open front portion includes outer front portions each extending from the outer side portions and defining a central front open portion. The four protrusions are arranged in a rectangle on an inside surface of the probe holder and are configured to suspend a wireless ultrasound probe within the probe holder.

20 Claims, 9 Drawing Sheets

ULTRASOUND PROBE HANGER AND METHOD FOR SUSPENDING A WIRELESS ULTRASOUND TRANSDUCER WITHIN A CHAMBER OF AN ULTRASOUND TRANSDUCER HIGH-LEVEL DISINFECTION (HLD) SYSTEM

FIELD

Certain embodiments relate to ultrasound transducer disinfection. More specifically, certain embodiments provide an ultrasound probe hanger operable to suspend a wireless ultrasound transducer in a chamber of an ultrasound transducer high-level disinfection (HLD) system during a disinfection cycle.

BACKGROUND

Ultrasound transducer high-level disinfection (HLD) systems, such as the TROPHON EPR and TROPHON 2 by NANOSONICS, typically include an enclosure having a top side, a bottom side, a left side, a right side, a front side, and a rear side. The front side may include an openable door providing access to a chamber within the enclosure. The top side may include an opening having an attachment mechanism for receiving and securing an ultrasound transducer cable such that the ultrasound probe is suspended by the cable within the chamber during disinfection. However, the attachment mechanism of existing ultrasound transducer HLD systems is not suitable for receiving and suspending a wireless ultrasound transducer within the chamber of the ultrasound transducer HLD system.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

An ultrasound probe hanger and method for suspending a wireless ultrasound transducer within a chamber of an ultrasound transducer HLD system is provided, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
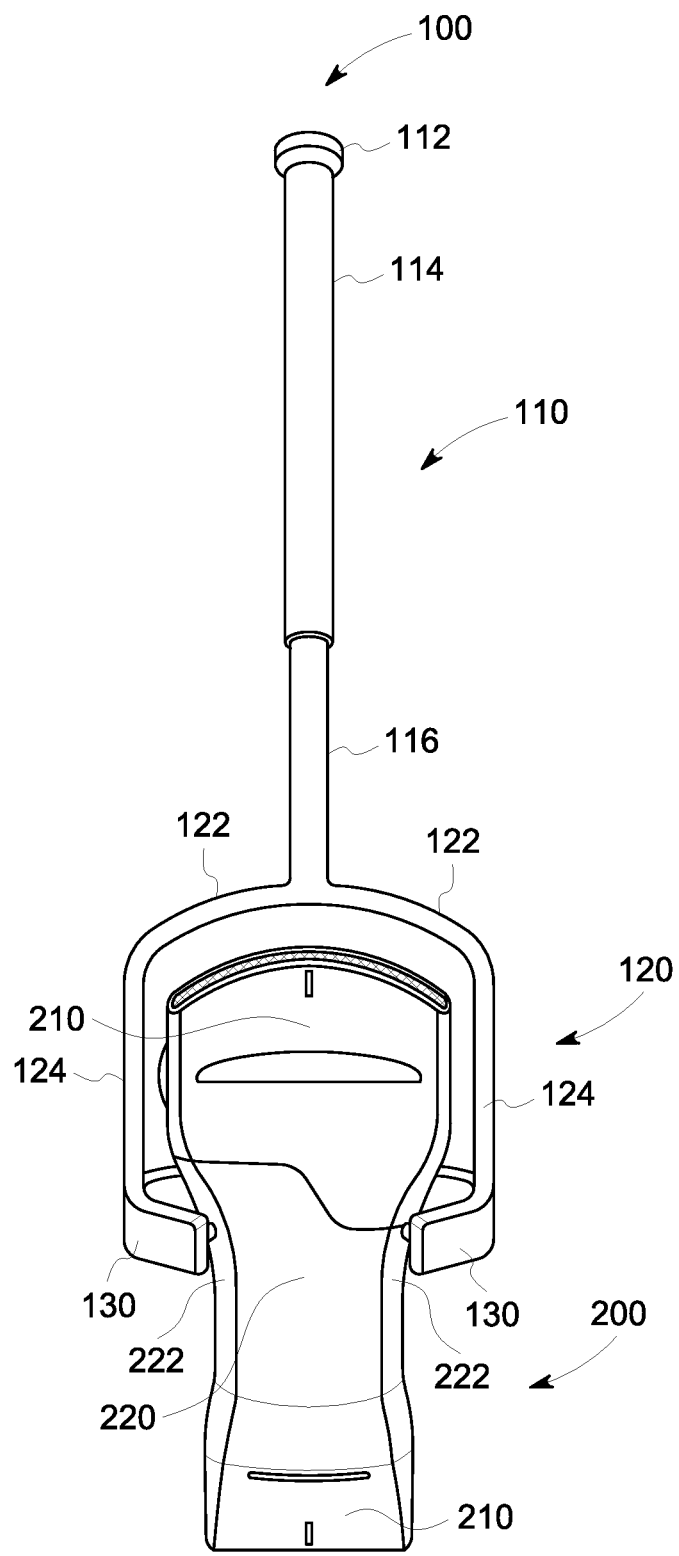
FIG. 1 illustrates a front, elevation view of an exemplary ultrasound probe hanger suspending a wireless ultrasound probe, in accordance with various embodiments.

Certain embodiments may be found in a method and system for suspending a wireless ultrasound transducer within a chamber of an ultrasound transducer HLD system. Aspects of the present disclosure provide the technical effect of allowing a wireless ultrasound probe to be suspended within a chamber of an ultrasound transducer HLD system during a disinfection cycle. Various embodiments provide a wireless ultrasound probe hanger having minimal contact points with the wireless ultrasound probe.

The foregoing summary, as well as the following detailed description of certain embodiments will be better understood when read in conjunction with the appended drawings. It should be understood that the various embodiments are not limited to the arrangements and instrumentality shown in the drawings. It should also be understood that the embodiments may be combined, or that other embodiments may be utilized and that structural changes may be made without departing from the scope of the various embodiments of the present disclosure. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Figure 2:
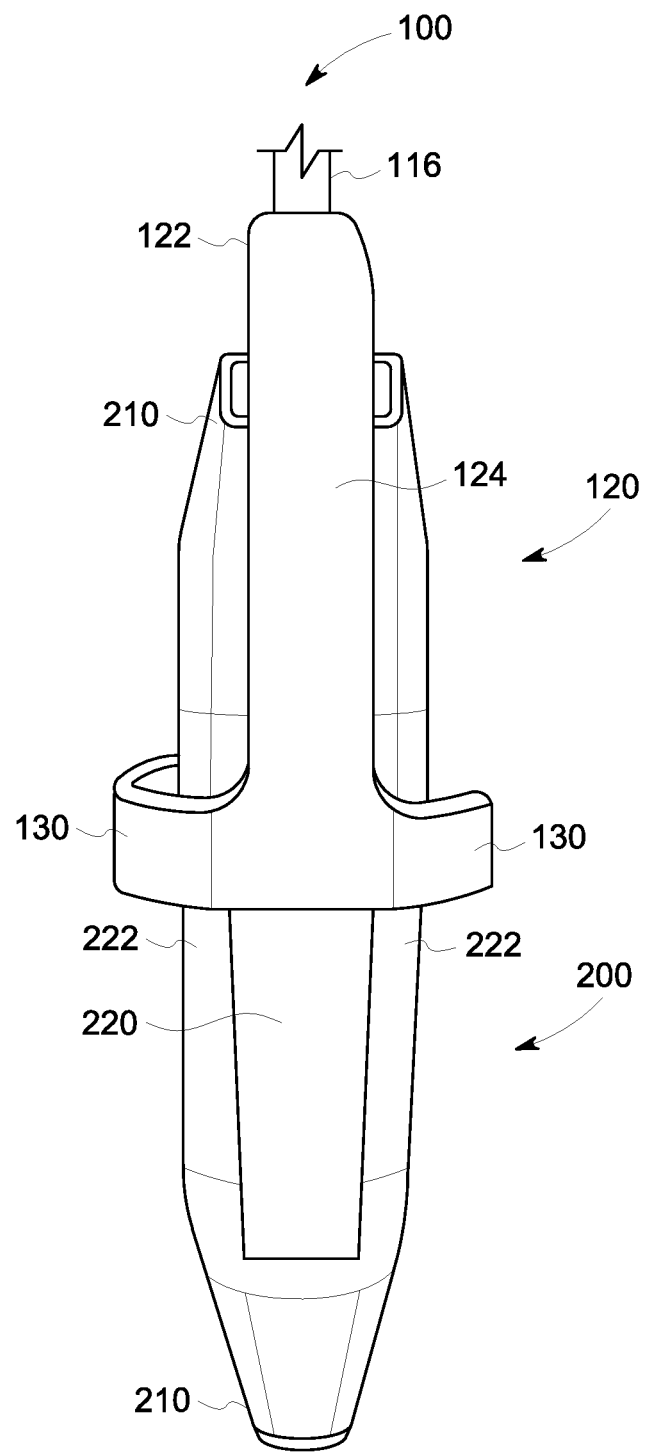
FIG. 2 illustrates a side, elevation view of an exemplary ultrasound probe hanger suspending a wireless ultrasound probe, in accordance with various embodiments.
Figure 3:
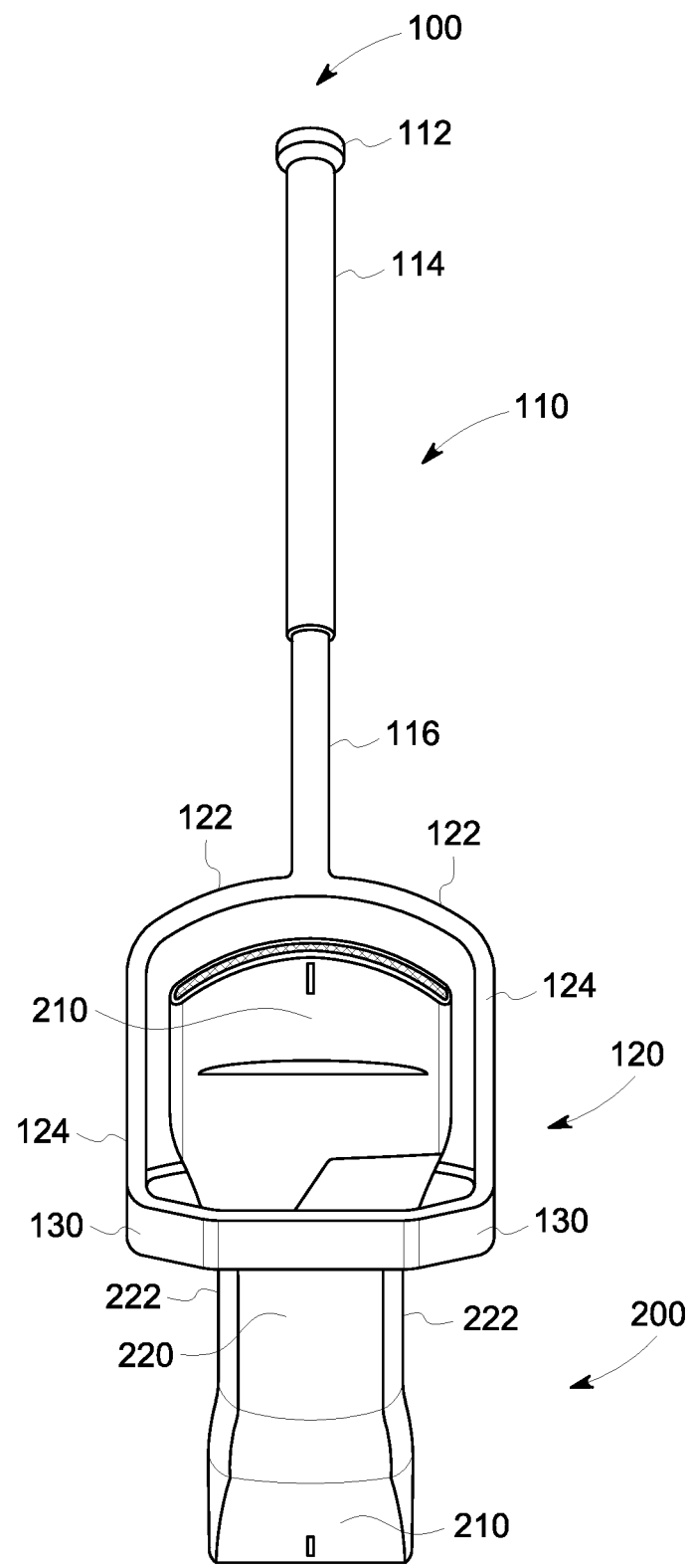
FIG. 3 illustrates a rear, elevation view of an exemplary ultrasound probe hanger suspending a wireless ultrasound probe, in accordance with various embodiments.
Figure 9:
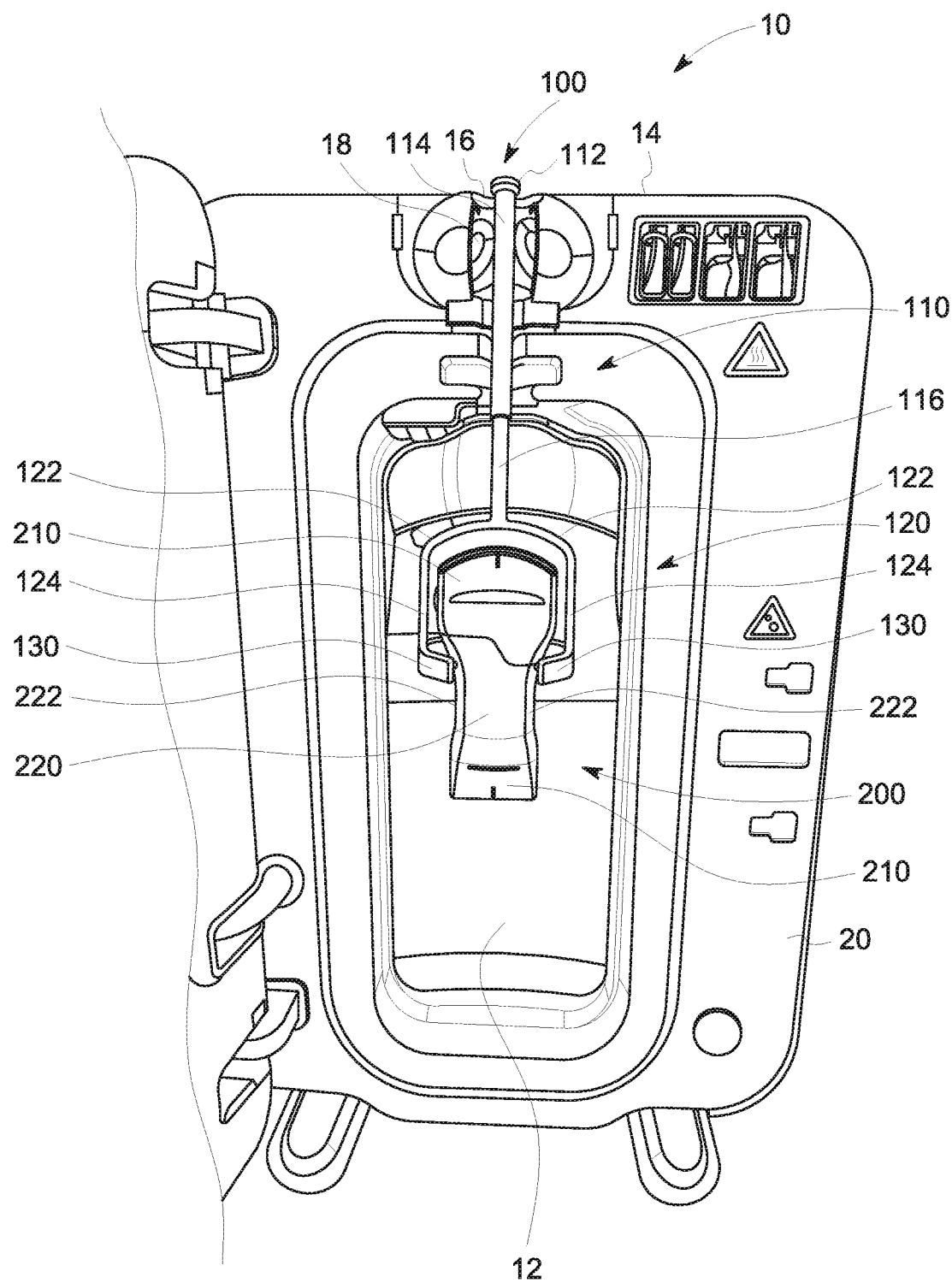
FIG. 9 illustrates a front, perspective view of an exemplary ultrasound transducer high-level disinfection (HLD) system open to expose a chamber having an ultrasound probe hanger suspending a wireless ultrasound probe disposed therein, in accordance with various embodiments.

FIG. 1 illustrates a front, elevation view of an exemplary ultrasound probe hanger 100 suspending a wireless ultrasound probe 200, in accordance with various embodiments. FIG. 2 illustrates a side, elevation view of an exemplary ultrasound probe hanger 100 suspending a wireless ultrasound probe 200, in accordance with various embodiments. FIG. 3 illustrates a rear, elevation view of an exemplary ultrasound probe hanger 100 suspending a wireless ultrasound probe 200, in accordance with various embodiments. FIG. 9 illustrates a front, perspective view of an exemplary ultrasound transducer high-level disinfection (HLD) system 10 open to expose a chamber 12 having an ultrasound probe hanger 100 suspending a wireless ultrasound probe 200 disposed therein, in accordance with various embodiments. Referring to FIGS. 1-3 and 9, an ultrasound probe hanger 100 disposed in a chamber (i.e., cavity) 12 of an HLD system 10 and suspending a wireless ultrasound probe 200 is shown. The HLD system comprises an enclosure (i.e., housing) 20 having a chamber 12 disposed therein. The HLD system 10 is configured to perform a disinfection cycle on an ultrasound probe 200 suspended inside the chamber 12. A top side 14 of the HLD system 10 comprises an opening 16 having an attachment mechanism 18 configured to receive an ultrasound probe hanger 100 holding a wireless ultrasound probe 200 or a probe cable of a wired ultrasound probe. The ultrasound probe hanger 100 may comprise a stem 110 and a lower hanger portion 120. The stem 110 may comprise a knob 112, an upper stem portion 114, and a lower stem portion 116. The knob 112 may be at a distal end of the stem 110 and may have a diameter (e.g., approximately 15 millimeters) that is greater than the diameter of the upper 114 and lower 116 stem portions. The knob 112 may be configured to be positioned abutting or outside the top side 14 of an ultrasound transducer HLD system 10 adjacent the opening 16 when the hanger 100 is attached within an HLD system 10. For example, the knob 112 may cover an opening 16 in the top side 14 of the HLD system 10 when the hanger 100 is attached within the HLD system 10. The upper stem portion 114 may extend from the knob 112 and may have an approximately ten (10) millimeter diameter of a standard ultrasound cable. The upper stem portion 114 may be configured to be received at an attachment mechanism 18 of the HLD system 10 that typically attaches to the cable of an ultrasound transducer. The lower stem portion 116 extends from the upper stem portion 114 to a proximal end of the stem 110. The lower stem portion 116 may be integrated with and/or attached to the lower hanger portion 120 at the proximal end of the stem 110. The lower stem portion 116 may be a same diameter as the upper stem portion 114, a greater diameter than the upper stem portion 114, or preferably, a smaller diameter than the upper stem portion 114 to minimize interference with a disinfection cycle of the HLD system 10, for example.

The lower hanger portion 120 may comprise shoulders 122, arms 124, and a probe holder 130. The shoulders 122 may be attached and/or integrated with the lower stem portion 116 at the proximal end of the stem 110. The shoulders 122 extend outward from and may be generally perpendicular to a longitudinal axis of the stem 110. In various embodiments, in addition to extending outward in a generally perpendicular direction from the longitudinal axis of the stem 110, the shoulders 122 may be arched or angled slightly downward (i.e., away) from the stem 110. For example, a central portion of the shoulders 122 may be attached and/or integrated with (i.e., connected to) the lower stem portion 116 and may be generally perpendicular to the longitudinal axis of the stem 110. Outer portions of the shoulders 122 may be arched or angled away from (i.e., downward from) the stem 110. The outer ends of the shoulder 122 may be attached to and/or integrated with arms 124 that each extend away from (i.e., downward from) the shoulders 122 and stem 110. The longitudinal axis of each of the arms 124 may be substantially parallel to each other and to the longitudinal axis of the stem 110. The upper ends of arms 124 are attached to and/or integrated with the outer ends of shoulders 122. The lower ends of arms 124 are attached to and/or integrated with the probe holder 130.

The probe holder 130 of the lower hanger portion 120 of the ultrasound probe hanger 100 may be generally-shaped as an open, horizontally-elongated hexagon shape or an open, horizontally-elongated oval shape having a continuous rear portion connected to (i.e., attached to and/or integrated with) a partially-open front portion at outer side portions. Each of the outer side portions of the probe holder 130 are attached to and/or integrated with one of the arms 124. The rear portion of the probe holder 130 extends from one of the outer side portions to the opposite outer side portion of the probe holder 130. The rear portion may be arched or angled. For example, the rear portion may include a central rear portion and outer rear portions. Each of the outer rear portions may be attached to and/or integrated with the outer side portions and may arch or angle rearward toward the central rear portion. The partially-open front portion may include outer front portions each attached to and/or integrated with the outer side portions and each arching or angling frontward toward a central front open portion. The combination of the outer side portions, the rear portion, and the front portion of the probe holder 130 may be generally C-shaped. The probe holder 130 may be configured to receive an upright wireless ultrasound probe 200 manipulated sideways through the central front open portion. The upright wireless ultrasound probe 200 may then be rotated 90 degrees within the probe holder 130 and placed on contact points on an inside surface of the probe holder 130, as described in more detail below.

The ultrasound probe hanger 100 may be a same material as an ultrasound probe body (i.e., housing) or any suitable material. For example, the ultrasound probe hanger 100 may be VALOX 357 by SABIC, which is a non-reinforced, impact modified, injection moldable grade resin (i.e., Polycarbonate/Polybutylene Terephthalate (PC/PBT)). In a representative embodiment, the ultrasound probe hanger 100 is a single integrated apparatus.

The wireless ultrasound probe 200 may comprise at least one transducer head 210 and a probe body 220. The at least one transducer head 210 may include, for example, a two dimensional (2D) array of piezoelectric elements. A group of transmit transducer elements and a group of receive transducer elements that normally constitute the same elements may be disposed within the at least one transducer head 210 and/or probe body 220. In certain embodiment, the ultrasound probe 200 may be operable to acquire ultrasound image data. The ultrasound image data may be wirelessly transmitted from the ultrasound probe 200 to one or more processors of an ultrasound machine. Control signals may be wirelessly transmitted by the ultrasound machine to the ultrasound probe 200. The probe body 220 may be a housing configured to be held by a user performing an ultrasound scan or otherwise manipulating the ultrasound probe 200. The probe body 220 may comprise corner portions 222. The wireless ultrasound probe 200 may be placed in the probe holder 130 of the ultrasound probe hanger 100 for disinfection in an ultrasound transducer HLD system 10 after or before use. In various embodiments, only four (4) contact points 132 of the probe holder 130 of the ultrasound probe hanger 100 contact the corner portions 222 of the probe body 220 of the wireless ultrasound probe 200 to suspend the wireless ultrasound probe 200 in the ultrasound transducer HLD system 10.

Figure 4:
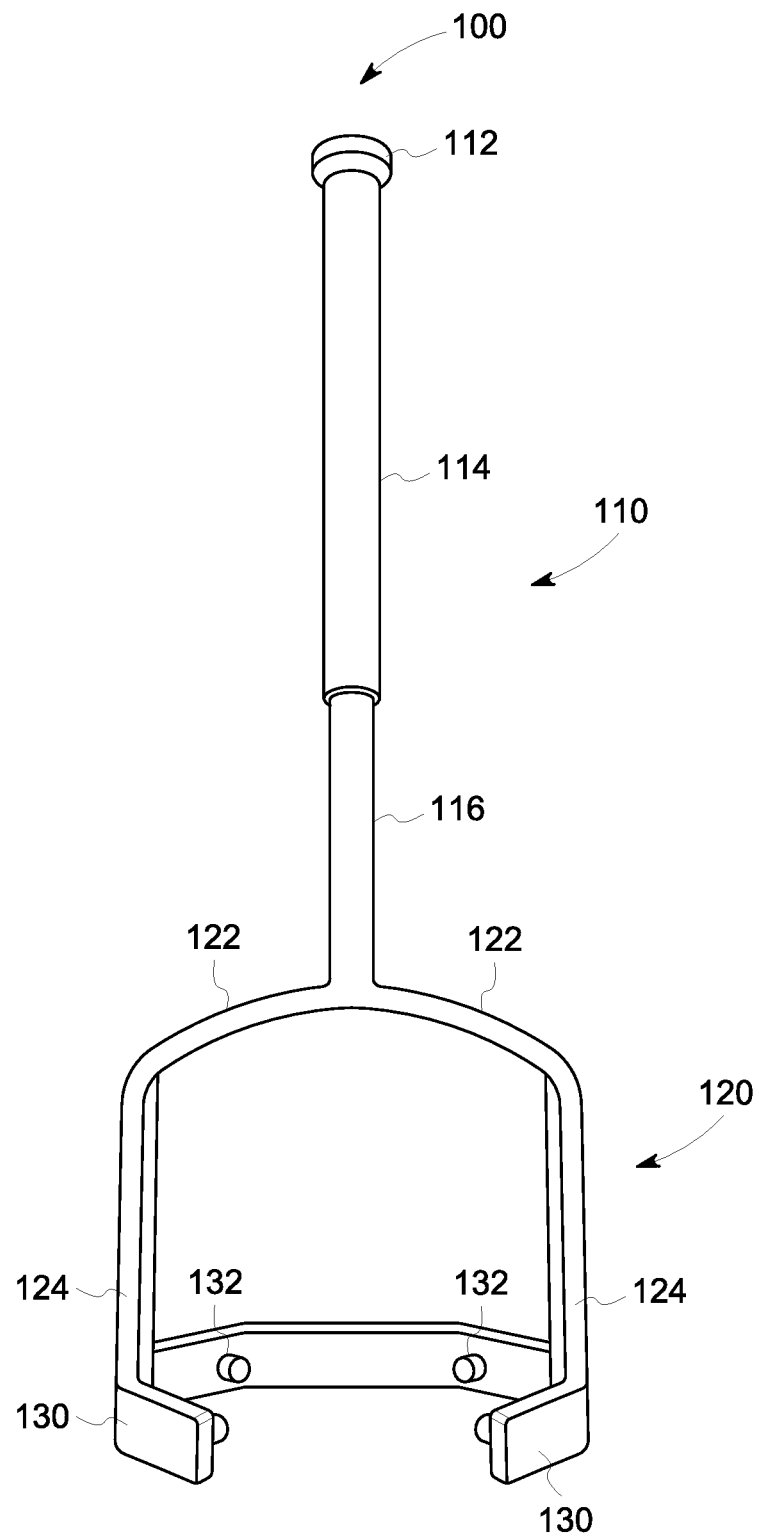
FIG. 4 illustrates a front, elevation view of an exemplary ultrasound probe hanger, in accordance with various embodiments.
Figure 5:
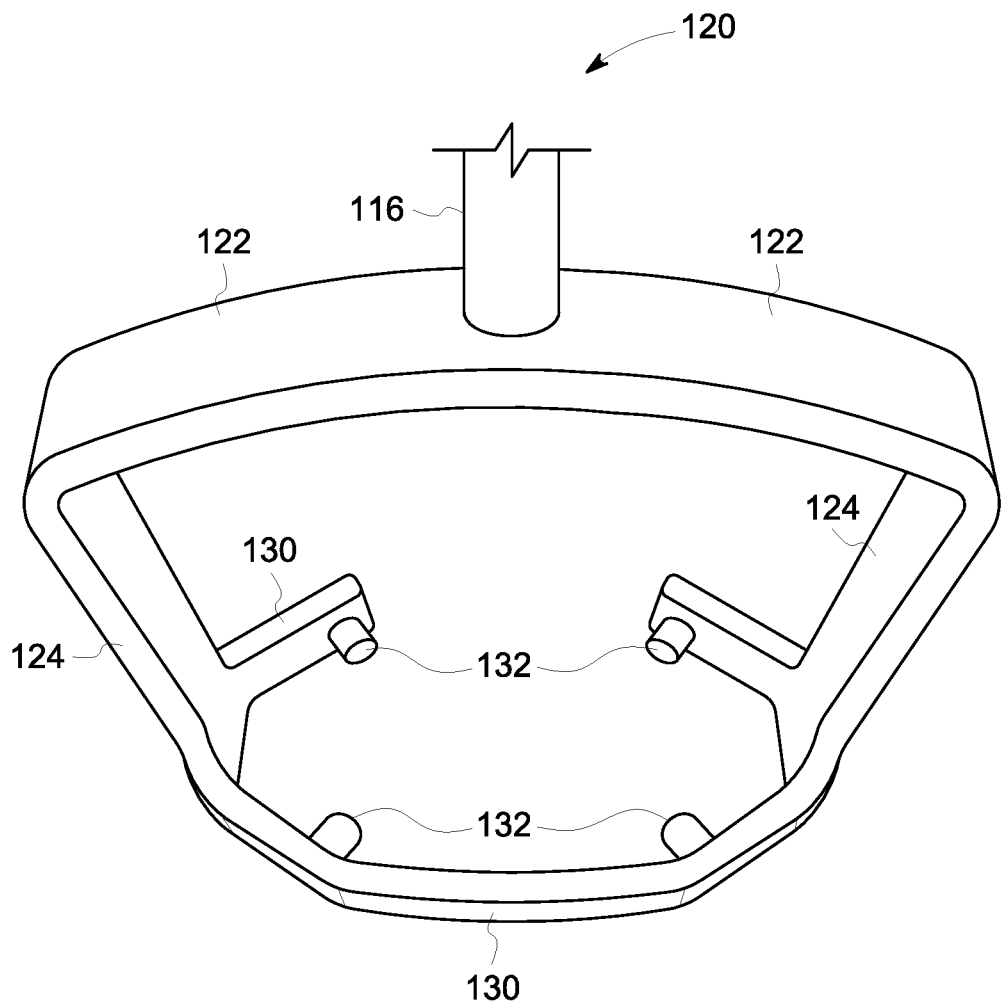
FIG. 5 illustrates a rear, perspective view of an exemplary lower hanger portion of an exemplary ultrasound probe hanger, in accordance with various embodiments.
Figure 6:
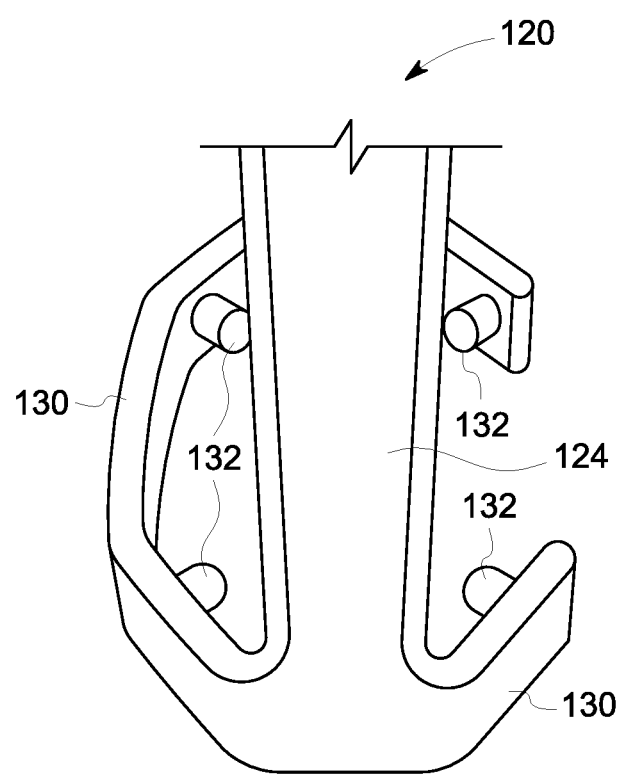
FIG. 6 illustrates a side, perspective view of an exemplary lower hanger portion of an exemplary ultrasound probe hanger, in accordance with various embodiments.
Figure 7:
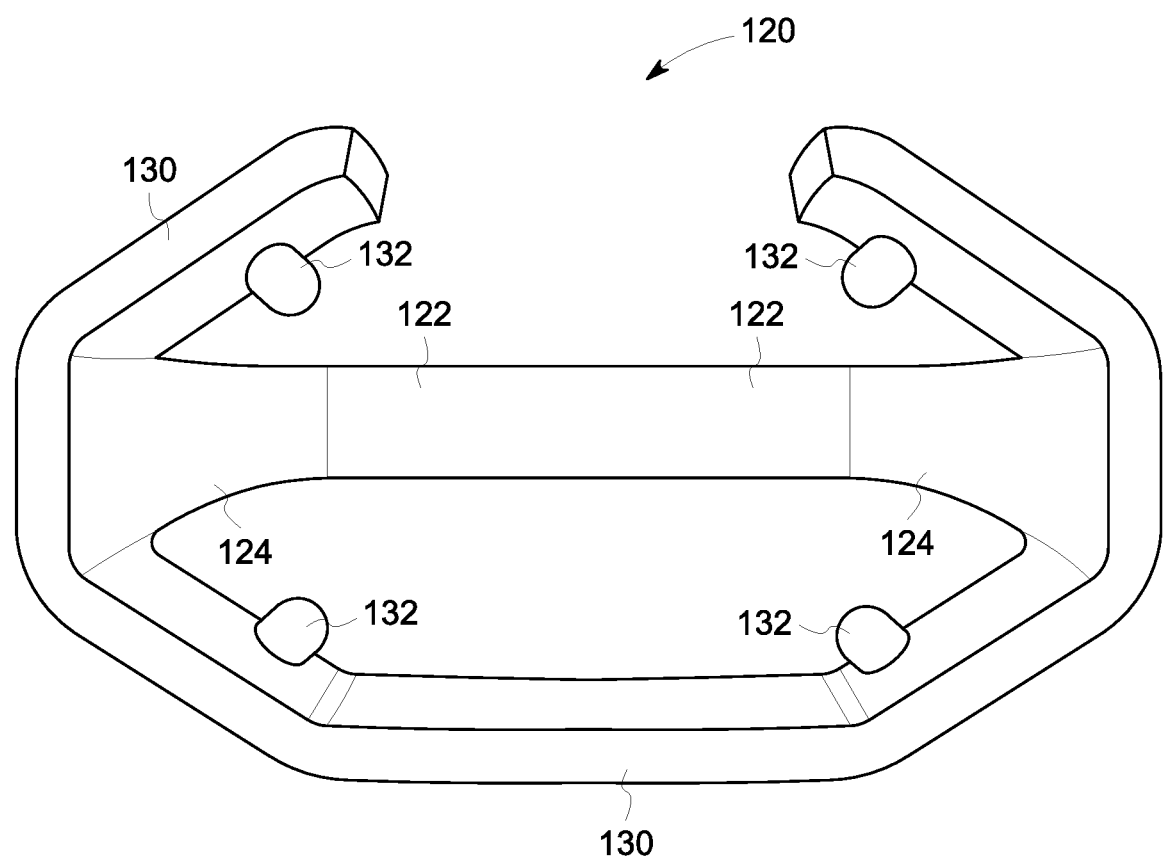
FIG. 7 illustrates a bottom, elevation view of an exemplary lower hanger portion of an exemplary ultrasound probe hanger, in accordance with various embodiments.

FIG. 4 illustrates a front, elevation view of an exemplary ultrasound probe hanger 100, in accordance with various embodiments. FIG. 5 illustrates a rear, perspective view of an exemplary lower hanger portion 120 of an exemplary ultrasound probe hanger 100, in accordance with various embodiments. FIG. 6 illustrates a side, perspective view of an exemplary lower hanger portion 120 of an exemplary ultrasound probe hanger 100, in accordance with various embodiments. FIG. 7 illustrates a bottom, elevation view of an exemplary lower hanger portion 120 of an exemplary ultrasound probe hanger 100, in accordance with various embodiments. Referring to FIGS. 4-7, the ultrasound probe hanger 100 may comprise a stem 110 and a lower hanger portion 120. The stem 110 may comprise a knob 112, an upper stem portion 114, and a lower stem portion 116. The stem 110 may be approximately 16 centimeters (e.g., 14-18 centimeters) long. The knob 112 may be at a distal end of the stem 110 and may have a diameter (e.g., 1.2-2.0 centimeters) that is greater than the diameter of the upper 114 (e.g., 0.8-1.2 centimeters) and lower 116 (e.g., 0.8-1.2 centimeters) stem portions. The upper stem portion 114 may extend from the knob 112 and may be approximately 10 centimeters (e.g., 8-12 centimeters) long. The lower stem portion 116 extends from the upper stem portion 114 to a proximal end of the stem 110. The lower stem portion 116 may be integrated with and/or attached to the lower hanger portion 120 at the proximal end of the stem 110. The lower stem portion 116 may be approximately 6 centimeters (e.g., 4-8 centimeters) long.

The lower hanger portion 120 may comprise shoulders 122, arms 124, and a probe holder 130. The shoulders 122 may be attached and/or integrated with the lower stem portion 116 at the proximal end of the stem 110. The shoulders 122 extend outward from and may be generally perpendicular to a longitudinal axis of the stem 110. In certain embodiments, the shoulders may be arched and/or include portions that angle downward from the stem 110. The shoulders may be approximately 9 centimeters (e.g., 8-10 centimeters) wide with the an equal distance of approximately 4.5 centimeters (e.g., 4-5 centimeters) from a center of the stem 110 at the connection to the shoulders 122 to the outer ends of the shoulders 122. The outer ends of the shoulder 122 may be attached to and/or integrated with arms 124 that each extend downward (i.e., away) from the shoulders 122 and stem 110. The longitudinal axis of each of the arms 124 may be substantially parallel to each other and to the longitudinal axis of the stem 110. The upper ends of arms 124 are attached to and/or integrated with the outer ends of shoulders 122. The lower ends of arms 124 are attached to and/or integrated with the probe holder 130. The arms 124 may extend approximately 6.5 centimeters (e.g., 5-8 centimeters) downward from the outer ends of the shoulders 122.

The probe holder 130 of the lower hanger portion 120 of the ultrasound probe hanger 100 may be generally C-shaped with each of the arms 124 connected (i.e., integrated with and/or attached to) the top and bottom portions (i.e., the outer side portions of the probe holder 130) of the C-shape. The front portion of the generally C-shaped probe holder 130 includes the opening. The rear portion of the generally C-shaped probe holder 130 is continuous between the outer side portions of the probe holder 130. An inside surface of the generally C-shaped probe holder 130 may include four (4) protrusions 132 configured to contact and securely hold an ultrasound probe 200. The protrusions 132 may be ball protrusions or any suitable protrusion that provides a dot contact, as opposed to a line contact, with corner portions 222 of a wireless ultrasound probe body 220. The protrusions 132 are arranged in a rectangle on an inside surface of the probe holder 130. For example, the protrusions 132 may be positioned to extend from an inside surface of outer rear portions of the rear portion of the probe holder 130 and from an inside surface of outer front portions of the front portion of the probe holder 130, adjacent the central front open portion of the probe holder 130. The probe holder 130 may be configured to receive an upright wireless ultrasound probe 200 manipulated sideways through the central front open portion. The upright wireless ultrasound probe 200 may then be rotated 90 degrees within the probe holder 130 and securely placed on protrusions 132 on the inside surface of the probe holder 130.

The width of the shoulder 122, arm 124, and probe holder 130 pieces may be approximately 1.5 centimeters (e.g., 1-2 centimeters) and a thickness of the shoulder 122, arm, 124, and probe holder 130 pieces may be approximately 0.3 centimeters (0.1-0.5 centimeters). The ultrasound probe hanger 100 may be a same material as an ultrasound probe body (e.g., VALOX 357 by SABIC) or any suitable material. The ultrasound probe hanger 100 may be disposable after each user. In a preferred embodiment, the ultrasound probe hanger 100 may be reusable for at least 1000 disinfection cycles of an HLD system 10 prior to replacement.

The ultrasound probe hanger 100 illustrated in FIGS. 4-7 shares various characteristics with the ultrasound probe hanger 100 illustrated in FIGS. 1-3 as described above.

Figure 8:
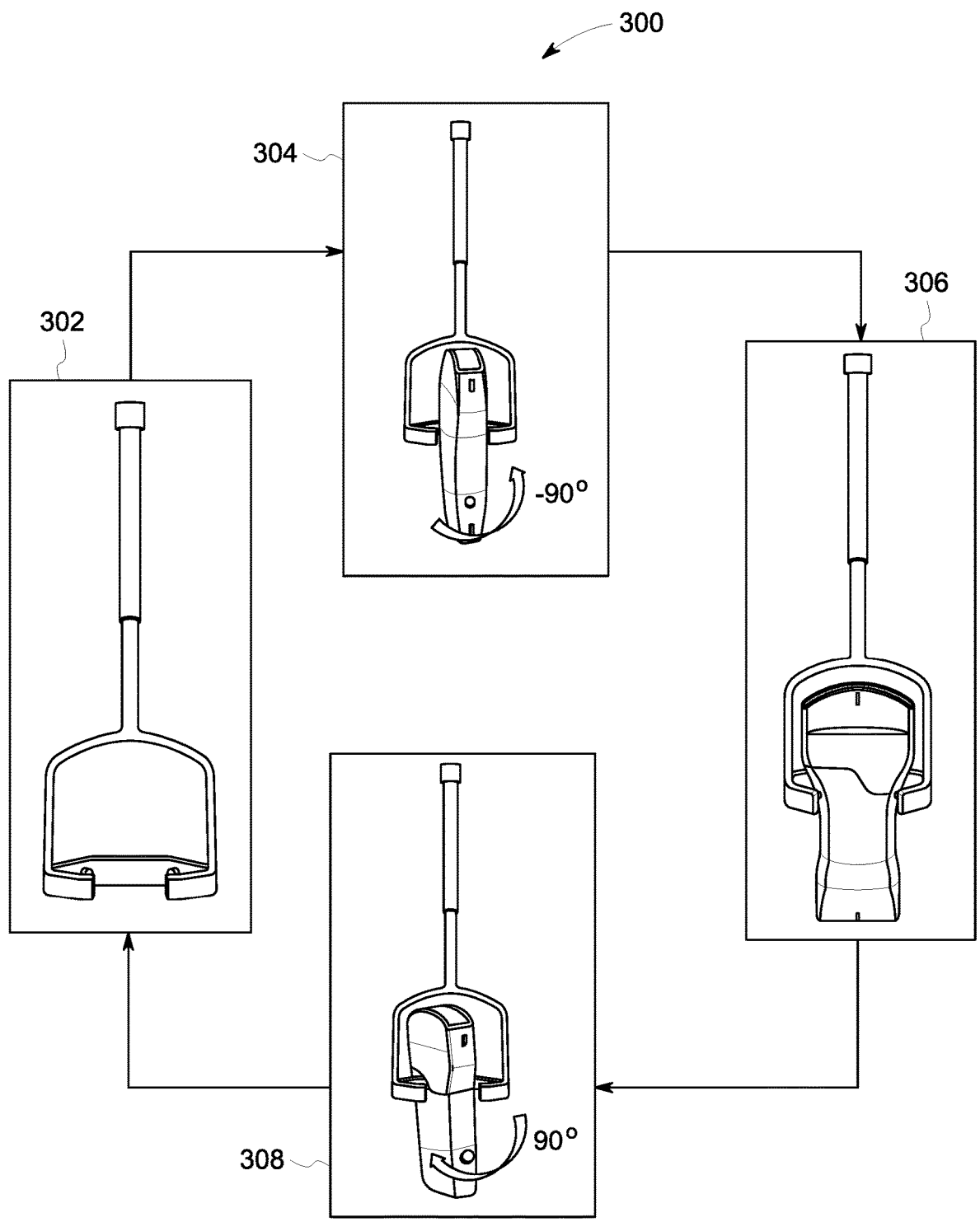
FIG. 8 is a flow diagram illustrating exemplary steps that may be utilized for suspending a wireless ultrasound transducer in an exemplary ultrasound probe hanger, in accordance with exemplary embodiments.

FIG. 8 is a flow diagram 300 illustrating exemplary steps 302-308 that may be utilized for suspending a wireless ultrasound transducer 200 in an exemplary ultrasound probe hanger 100, in accordance with exemplary embodiments. Referring to FIG. 8, there is shown a flow diagram 300 comprising exemplary steps 302 through 308.

At step 302, an ultrasound probe hanger 100 may be held upright by a user and/or inserted in into an ultrasound transducer HLD system 10 by coupling an upper stem portion 114 of a stem 110 of the hanger 100 to an attachment mechanism 18 of the HLD system 10. In various embodiments, the ultrasound probe hanger 100 may be inserted into the HLD system 10 after the wireless ultrasound probe 200 is secured within the probe holder 130 of the ultrasound probe hanger 100 at step 306.

At step 304, a wireless ultrasound probe 200 that is positioned upright and oriented substantially sideways may be moved into a probe holder 130 of the ultrasound probe hanger 100 through a central front open portion of the probe holder 130 and rotated approximately 90 degrees (i.e., 60-120 degrees) in either lateral direction within the probe holder 130.

At step 306, the wireless ultrasound probe 200 is secured against protrusions 132 on an inside surface of the probe holder 130 of the ultrasound probe hanger 100. For example, after rotating the probe 200 within the probe holder at step 304, the wireless ultrasound probe 200 may be lowered to securely rest on the protrusions 132 of the probe holder 130. The protrusions 132 may be four (4) contact points arranged in a rectangle that provide a dot contact with corner portions 222 of the probe body 220 of the wireless ultrasound probe 200. The four protrusion dot contacts with the wireless ultrasound probe 200 minimize an amount of contact with the ultrasound probe 200 to maximize the surface area of the ultrasound probe 200 that can be disinfected. The minimum contact of the ultrasound probe hanger 100 with the wireless ultrasound probe 200 may allow the wireless ultrasound probe 200 to be effectively disinfected in one cleaning cycle of the HLD system 10. If the ultrasound probe hanger 100 was inserted into the HLD system 10 at step 302, the HLD system 10 may be operated to disinfect the wireless ultrasound probe 200 at step 306. If the ultrasound probe hanger 100 has not yet been inserted into the HLD system 10, the ultrasound probe hanger 100 securely holding the wireless ultrasound probe 200 may be inserted into the HLD system 10 by coupling the upper stem portion 114 of the stem 110 of the hanger 100 to an attachment mechanism 18 of the HLD system 10 prior to performing a disinfection cycle.

At step 308, the disinfected wireless ultrasound probe 200 may be removed from the ultrasound probe hanger 100 after the cleaning cycle is performed by the HLD system 10. For example, the wireless ultrasound probe 200 may be lifted off the protrusions 132 on the inside surface of the probe holder 130 and rotated approximately 90 degrees (i.e., 60-120 degrees) in either lateral direction within the probe holder 130. The wireless ultrasound probe 200 in the rotated (i.e., substantially sideways) orientation may be moved through the central front open portion of the probe holder 130 to remove the wireless ultrasound probe 200 from the ultrasound probe hanger 100 leaving the empty ultrasound probe hanger of step 302. The disinfected wireless ultrasound probe 200 is then ready for use and the empty ultrasound probe hanger 100 is ready to receive a wireless ultrasound probe 200 for disinfection in the HLD system 10.

Aspects of the present disclosure provide an ultrasound probe hanger 100 operable to suspend a wireless ultrasound transducer 200 in a chamber of an ultrasound transducer high-level disinfection (HLD) system 10 during a disinfection cycle. The ultrasound probe hanger 100 may comprise a stem 110, shoulders 122, arms 124, and a probe holder 130. The stem 110 may have a distal end, a proximal end, and a longitudinal axis. The shoulders 122 may be arranged generally perpendicular to the longitudinal axis of the stem 110. The shoulders 122 may comprise a central shoulder portion and outer shoulder portions. Each of the outer shoulder portions may have an outer shoulder end. The central shoulder portion may be connected to proximal end of the stem 110. The arms 124 may be arranged generally parallel to each other and to the longitudinal axis of the stem 110. Each of the arms 124 may have an upper end and a lower end. The upper end of each of the arms 124 may be connected to the outer shoulder end of a different one of the outer shoulder portions of the shoulders 122. The probe holder 130 may comprise outer side portions, a rear portion, a partially-open front portion, and four (4) protrusions 132. Each of the outer side portions may be connected to the lower end of a different one of the arms 124. The rear portion may comprise outer rear portions and a central rear portion. The rear portion may extend between and connect the outer side portions. The partially-open front portion may comprise outer front portions and a central front open portion. The outer front portions may each extend from a different one of the outer side portions to the central front open portion. The four (4) protrusions 132 may be arranged in a rectangle on an inside surface of the outer rear portions and outer front portions. The four protrusions 132 may be configured to contact corner portions 222 of a wireless ultrasound probe 200 to securely suspend the wireless ultrasound probe 200 within the probe holder 130.

In a representative embodiment, the stem 110 may comprise a knob 112 at the distal end, a lower stem portion 116 at the proximal end, and an upper stem portion 114 extending between the knob 112 and the lower stem portion 116. A knob diameter may be greater than an upper stem portion diameter and a lower stem portion diameter. In an exemplary embodiment, the upper stem portion diameter is approximately 10 millimeters. In various embodiments, the lower stem portion diameter is less than the upper stem portion diameter. In certain embodiments, the outer shoulder portions are one or more of arched or angled away from stem 110. In a representative embodiment, the arms 124 extend from the outer shoulder ends in a direction away from the stem 110. In an exemplary embodiment, the probe holder 130 is generally shaped as one or more of an open, horizontally-elongated hexagon shape, or an open, horizontally-elongated oval shape. In various embodiments, the probe holder 130 is generally C-shaped. In certain embodiments, the four protrusions 132 are ball protrusions. In certain embodiments, each of the four protrusions 132 is configured to provide a dot contact with a different corner portion 222 of the wireless ultrasound probe 200. In a representative embodiment, each of the four protrusions 132 provide a corner of the rectangle. A first of the four protrusions 132 is positioned on an inside surface of a first outer rear portion of the rear portion. A second of the four protrusions 132 is positioned on an inside surface of a second outer rear portion of the rear portion on an opposite side of the central rear portion. A third of the four protrusions 132 is positioned on an inside surface of a first outer front portion of the partially-open front portion across from the first outer rear portion. A fourth of the four protrusions 132 is positioned on an inside surface of a second outer front portion of the partially-open front portion across from the second outer rear portion and on an opposite side of the central front open portion from the first outer front portion. In an exemplary embodiment, the ultrasound probe hanger 100 is a single, integrated apparatus. In certain embodiments, the ultrasound probe hanger 100 is VALOX 357.

Various embodiments provide a method 300 for suspending a wireless ultrasound probe 200 in an ultrasound probe hanger 100. The method 300 may comprise moving 304 the wireless ultrasound probe 200 positioned upright and rotated sideways through a central front open portion of a probe holder 130 of the ultrasound probe hanger 100. The wireless ultrasound probe 200 may comprise at least one transducer head 210 and a probe body 220. The probe body 220 may comprise corner portions 222. The ultrasound probe hanger 100 may comprise a stem 110 having a distal end, a proximal end, and a longitudinal axis. The ultrasound probe hanger 100 may comprise shoulders 122 arranged generally perpendicular to the longitudinal axis of the stem 110. The shoulders 122 may comprise a central shoulder portion and outer shoulder portions. Each of the outer shoulder portions may have an outer shoulder end. The central shoulder portion may be connected to proximal end of the stem 110. The ultrasound probe hanger 100 may comprise arms 124 arranged generally parallel to each other and to the longitudinal axis of the stem 110. Each of the arms 124 may have an upper end and a lower end. The upper end of each of the arms 124 may be connected to the outer shoulder end of a different one of the outer shoulder portions of the shoulders 122. The ultrasound probe hanger 100 may comprise the probe holder 130. The probe holder 130 may comprise outer side portions, a rear portion, a partially-open front portion, and four (4) protrusions 132. Each of the outer side portions may be connected to the lower end of a different one of the arms 124. The rear portion may comprise outer rear portions and a central rear portion. The rear portion may extend between and connect the outer side portions. The partially-open front portion may comprise outer front portions and the central front open portion. The outer front portions may each extend from a different one of the outer side portions to the central front open portion. The four (4) protrusions 132 may be arranged in a rectangle on an inside surface of the outer rear portions of the rear portion and the outer front portions of the partially-open front portion. The method 300 may comprise rotating 304 the wireless ultrasound probe 200 approximately ninety (90) degrees within the probe holder 130. The method 300 may comprise placing 306 the corner portions 222 of the probe body 220 of the wireless ultrasound probe 200 on the four protrusions 132 of the probe holder 130 to securely suspend the wireless ultrasound probe 200 within the probe holder 130.

In an exemplary embodiment, the upright positioning of the wireless ultrasound probe 200 is with the at least one transducer head 210 facing upward. In various embodiments, the stem 110 comprises a knob 112 at the distal end, a lower stem portion 116 at the proximal end, and an upper stem portion 114 extending between the knob 112 and the lower stem portion 116. In certain embodiments, the method 300 further comprises coupling 302, 306 the upper stem portion 114 of the stem 110 of the ultrasound probe hanger 100 to an attachment mechanism 18 of an ultrasound transducer high-level disinfection (HLD) system 10. The method 300 may further comprise performing 306 a disinfection cycle of the HLD system 10 with the wireless ultrasound probe 200 suspended in the ultrasound probe hanger 100 in a cavity 12 of the HLD system 10. In a representative embodiment, the method 300 may further comprise removing 308, 302 the wireless ultrasound probe 200 from the ultrasound probe hanger 100 by lifting 308 the wireless ultrasound probe 200 off the four protrusions 132 of the probe holder 130, rotating 308 the wireless ultrasound probe 200 approximately ninety (90) degrees within the probe holder 130, and moving 308 the wireless ultrasound probe 200 out of the probe holder 130 of the ultrasound probe hanger 100 through the central front open portion of the probe holder 130. In an exemplary embodiment, the probe holder 130 is one or more of an open, horizontally-elongated hexagon shape; an open, horizontally-elongated oval shape; or, generally C-shaped. In various embodiments, the ultrasound probe hanger 100 is a same material as the probe body 220 of the wireless ultrasound probe 200.

As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, a component is "operable" or "configured" to perform a function whenever the component comprises the necessary structure to perform the function, regardless of whether performance of the function is disabled, or not enabled, by some user-configurable setting.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. An ultrasound probe hanger comprising:
   a stem having a distal end, a proximal end, and a longitudinal axis;
   shoulders extending away from the longitudinal axis of the stem, the shoulders comprising a central shoulder portion and outer shoulder portions, each of the outer shoulder portions having an outer shoulder end, the central shoulder portion connected to proximal end of the stem;
   arms arranged parallel to each other, each of the arms having an upper end and a lower end, the upper end of each of the arms connected to the outer shoulder end of a different one of the outer shoulder portions of the shoulders; and
   a probe holder comprising:
      outer side portions, each of the outer side portions connected to the lower end of a different one of the arms,
      a rear portion comprising outer rear portions and a central rear portion, the rear portion extending between and connecting the outer side portions,
      a partially-open front portion comprising outer front portions and a central front open portion, the outer front portions each extending from a different one of the outer side portions to the central front open portion, and
      four protrusions arranged in a rectangle on an inside surface of the outer rear portions and outer front portions, the four protrusions configured to contact corner portions of a wireless ultrasound probe to securely suspend the wireless ultrasound probe within the probe holder.

2. The ultrasound probe hanger of claim 1, wherein the stem comprises a knob at the distal end, a lower stem portion at the proximal end, and an upper stem portion extending between the knob and the lower stem portion, wherein a knob diameter is greater than an upper stem portion diameter and a lower stem portion diameter.

3. The ultrasound probe hanger of claim 2, wherein the upper stem portion diameter is 10 millimeters.

4. The ultrasound probe hanger of claim 2, wherein the lower stem portion diameter is less than the upper stem portion diameter.

5. The ultrasound probe hanger of claim 1, wherein the outer shoulder portions are one or more of arched or angled away from stem.

6. The ultrasound probe hanger of claim 1, wherein the arms extend from the outer shoulder ends in a direction away from the stem.

7. The ultrasound probe hanger of claim 1, wherein the probe holder is shaped as one or more of:
   an open, horizontally-elongated hexagon shape, or
   an open, horizontally-elongated oval shape.

8. The ultrasound probe hanger of claim 1, wherein the probe holder is C-shaped.

9. The ultrasound probe hanger of claim 1, wherein the four protrusions are ball protrusions.

10. The ultrasound probe hanger of claim 1, wherein each of the four protrusions is configured to provide a dot contact with a different corner portion of the wireless ultrasound probe.

11. The ultrasound probe hanger of claim 1, wherein each of the four protrusions provide a corner of the rectangle, and wherein:
   a first of the four protrusions is positioned on an inside surface of a first outer rear portion of the rear portion,
   a second of the four protrusions is positioned on an inside surface of a second outer rear portion of the rear portion on an opposite side of the central rear portion, a third of the four protrusions is positioned on an inside surface of a first outer front portion of the partially-open front portion across from the first outer rear portion, and a fourth of the four protrusions is positioned on an inside surface of a second outer front portion of the partially-open front portion across from the second outer rear portion and on an opposite side of the central front open portion from the first outer front portion.

12. The ultrasound probe hanger of claim 1, wherein the ultrasound probe hanger is a single, integrated apparatus.

13. The ultrasound probe hanger of claim 1, wherein the ultrasound probe hanger is VALOX 357.

14. A method for suspending a wireless ultrasound probe in an ultrasound probe hanger, the method comprising:
   moving the wireless ultrasound probe positioned upright and rotated sideways through a central front open portion of a probe holder of the ultrasound probe hanger, wherein the wireless ultrasound probe comprises at least one transducer head and a probe body, the probe body comprising corner portions, and wherein the ultrasound probe hanger comprises:
      a stem having a distal end, a proximal end, and a longitudinal axis;
      shoulders extending away from the longitudinal axis of the stem, the shoulders comprising a central shoulder portion and outer shoulder portions, each of the outer shoulder portions having an outer shoulder end, the central shoulder portion connected to proximal end of the stem;
      arms arranged parallel to each other, each of the arms having an upper end and a lower end, the upper end of each of the arms connected to the outer shoulder end of a different one of the outer shoulder portions of the shoulders; and
      the probe holder comprising:
         outer side portions, each of the outer side portions connected to the lower end of a different one of the arms,
         a rear portion comprising outer rear portions and a central rear portion, the rear portion extending between and connecting the outer side portions,
         a partially-open front portion comprising outer front portions and the central front open portion, the outer front portions each extending from a different one of the outer side portions to the central front open portion, and
         four protrusions arranged in a rectangle on an inside surface of the outer rear portions of the rear portion and the outer front portions of the partially-open front portion;
   rotating the wireless ultrasound probe 60 to 120 degrees within the probe holder; and
   placing the corner portions of the probe body of the wireless ultrasound probe on the four protrusions of the probe holder to securely suspend the wireless ultrasound probe within the probe holder.

15. The method of claim 14, wherein the upright positioning of the wireless ultrasound probe is with the at least one transducer head facing upward.

16. The method of claim 14, wherein the stem comprises a knob at the distal end, a lower stem portion at the proximal end, and an upper stem portion extending between the knob and the lower stem portion.

17. The method of claim 16, further comprising:
   coupling the upper stem portion of the stem of the ultrasound probe hanger to an attachment mechanism of an ultrasound transducer high-level disinfection (HLD) system; and
   performing a disinfection cycle of the HLD system with the wireless ultrasound probe suspended in the ultrasound probe hanger in a cavity of the HLD system.

18. The method of claim 17, further comprising removing the wireless ultrasound probe from the ultrasound probe hanger by:
   lifting the wireless ultrasound probe off the four protrusions of the probe holder;
   rotating the wireless ultrasound probe 60 to 120 degrees within the probe holder; and
   moving the wireless ultrasound probe out of the probe holder of the ultrasound probe hanger through the central front open portion of the probe holder.

19. The method of claim 14, wherein the probe holder is one or more of:
   an open, horizontally-elongated hexagon shape,
   an open, horizontally-elongated oval shape, or
   C-shaped.

20. The method of claim 14, wherein the ultrasound probe hanger is a same material as the probe body of the wireless ultrasound probe.

* * * * *